US00PP19848P3

(12) United States Plant Patent
Hambali

(10) Patent No.: US PP19,848 P3
(45) Date of Patent: Mar. 24, 2009

(54) ***AGLAONEMA* PLANT NAMED 'TWYAG0004'**

(50) Latin Name: *Aglaonema hybrid*
Varietal Denomination: TWYAG0004

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/784,627

(22) Filed: Apr. 9, 2007

(65) Prior Publication Data

US 2008/0250537 P1 Oct. 9, 2008

(51) Int. Cl.
*A01H 5/00* (2006.01)

(52) U.S. Cl. ..... Plt./376
(58) Field of Classification Search ..... Plt./376
See application file for complete search history.

*Primary Examiner*—Annette H Para
*Assistant Examiner*—Georgia Helmer
(74) *Attorney, Agent, or Firm*—Jondle & Associates, P.C.

(57) ABSTRACT

A new *Aglaonema* plant particularly distinguished by being intermediate in stature, leafy, compact, having an upright growth habit, and producing many basal branches and numerous leaves, is disclosed.

2 Drawing Sheets

Genus and species: *Aglaonema hybrid.*
Variety denomination: 'TWYAG0004'.

BACKGROUND OF THE NEW PLANT

The present invention comprises a new and distinct cultivar of *Aglaonema,* botanically known as *Aglaonema* hybrid, and hereinafter referred to by the cultivar name 'TWYAG0004'. The new cultivar originated from a hybridization made in Bogor, W. Java, Indonesia between *A. commutatum* var. *tricolor* (unpatented) and *A. rotundum* (unpatented) in October 1999.

The new cultivar was created in Bogor, W. Java, Indonesia and has been asexually reproduced repeatedly by vegetative cuttings and tissue culture in Apopka, Fla. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1. Intermediate in stature;
2. Leafy, compact and upright branched growth habit; and
3. Produces many basal branches and numerous leaves.

DESCRIPTION OF PHOTOGRAPHS

This new *Aglaonema* plant is illustrated by the accompanying photographs which show overall plant habit and the upper and lower surface of a mature leaf. The colors shown are as true as can be reasonably obtained by conventional photographic procedures.

Figure 1:
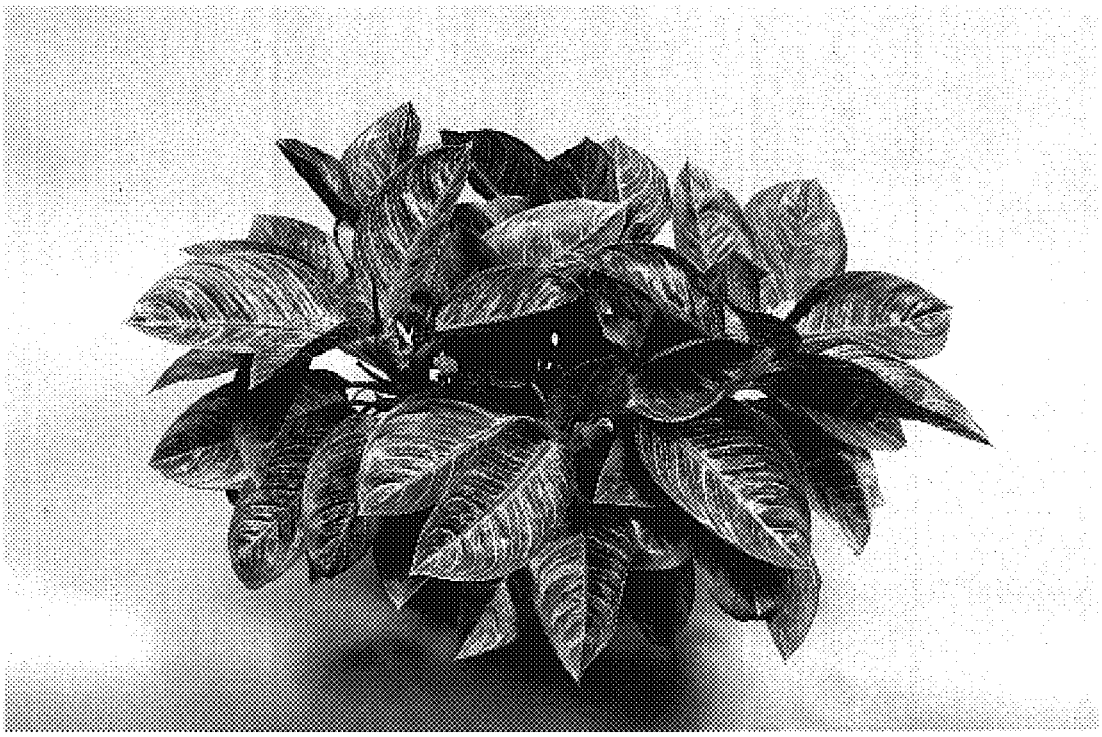

FIG. 1. shows the overall plant habit.

Figure 2:
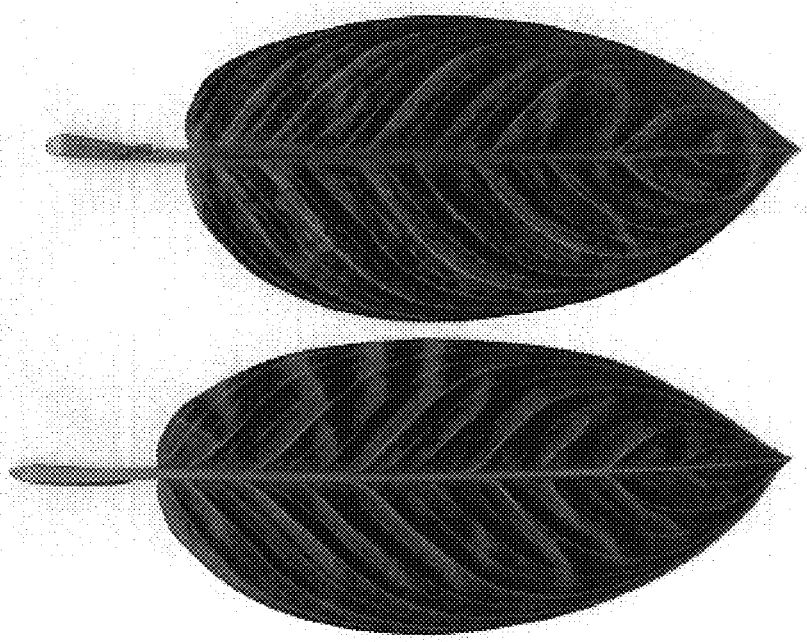

FIG. 2. shows the upper and lower surface of a mature leaf.

Figure 3:
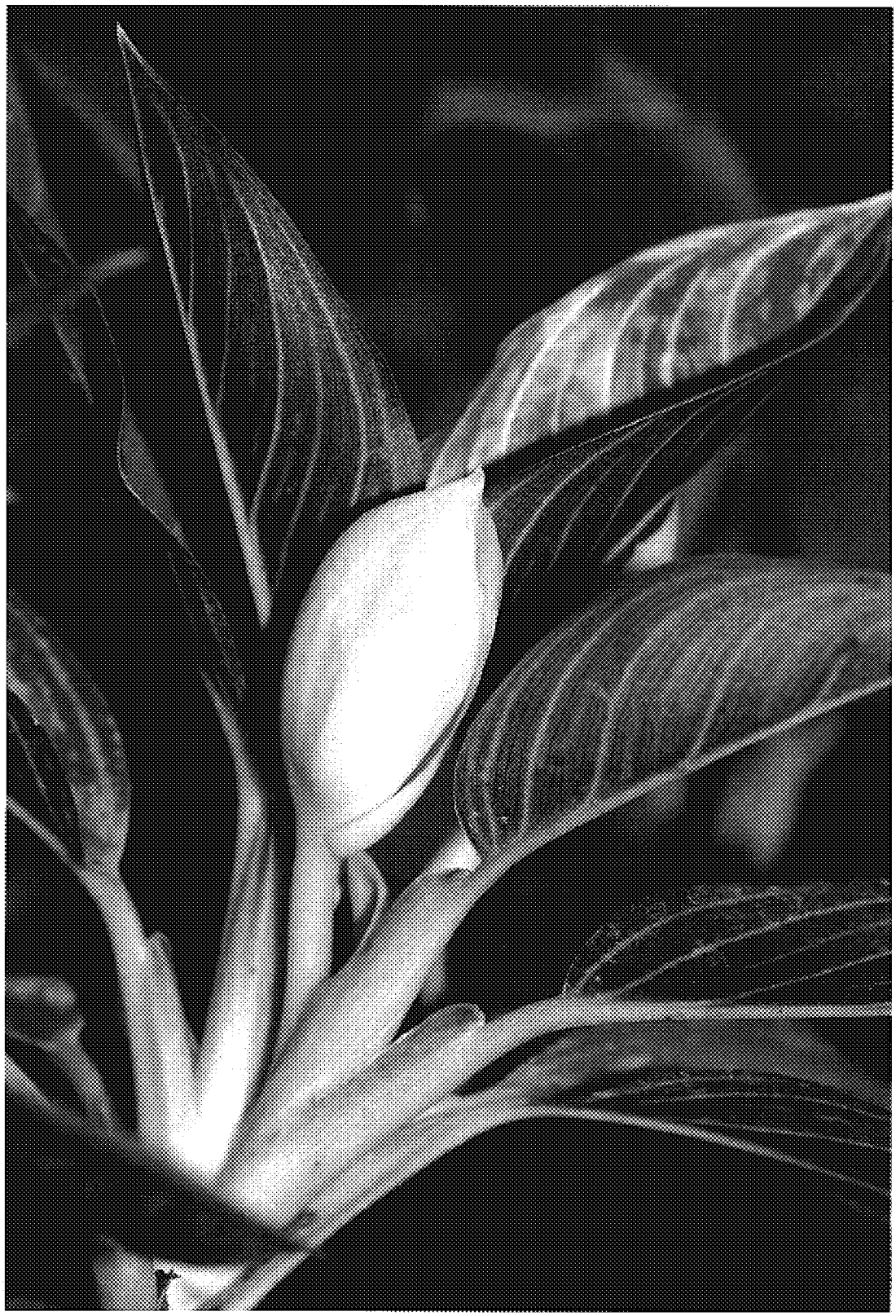

FIG. 3. shows a mature bud of an inflorescence.

The age of the plant in FIG. 1 and FIG. 2 is 10 months old. The age of the plant in FIG. 3 is 2 years old.

DESCRIPTION OF THE NEW CULTIVAR

The following detailed description sets forth the distinctive characteristics of 'TWYAG0004'. The data which define these characteristics were collected from asexual reproductions carried out in Apopka, Fla. The plant history was taken on 18-month-old plants started from a single four-leaf rooted cutting, still in a vegetative state and grown in Apopka, Fla. Rooted cuttings were planted in 20-cm pots and grown in a greenhouse in July 2006. The plants were pinched twice. Color readings were taken under natural light. Color references are primarily to the R.H.S. Colour Chart of The Royal Horticultural Society of London (R.H.S.) (2001).

DETAILED BOTANICAL DESCRIPTION

Classification:
- *Family.*—Araceae.
- *Botanical.*—*Aglaonema* hybrid.
- *Common name.*—Chinese Evergreen.

Parentage:
- *Female parent.*—*A. commutatum* var. *tricolor* (unpatented).
- *Male parent.*—*A. rotundum* (unpatented).

Growth:
- *Form.*—Symmetrical, wider than tall; new leaves held upright, mature leaves arch outward.
- *Growth and branching habit.*—Leafy and compact; upright, branched growth habit (basal branching); intermediate in stature.
- *Height* (*from soil to top of leaf plane*).—30 cm to 35 cm.
- *Diameter* (*area of spread, measured from leaf tip to leaf tip across the canopy*).—48 cm to 52 cm.
- *Time to produce a finished flowering plant.*—18 months starting from a single four-leaf rooted cutting and pinched twice.
- *Root description.*—Abundant fleshy white roots with finer lateral branches.
- *Number of divisions or clumps per year.*—About 6 to 10 four-leaf cuttings per year.

*Durability of foliage to stresses.*—Leaves hold up well against damage from shipping and handling; plant is durable, excellent indoor keeping quality.

*High temperature tolerance.*—To about 104° F. for several hours without damage.

*Low temperature tolerance.*—To about 55° F. for several hours without damage.

Stems:

*Number of branches per plant.*—23.

*Length (from soil line to the junction of the newest to leaves).*—15 cm.

*Diameter (measured from the midpoint).*—0.95 cm.

*Internode length.*—1.1 cm to 1.6 cm.

*Color.*—Immature: RHS 155B tinged with RHS 144C. Mature: RHS 161A to RHS 161B with areas of RHS 146B to RHS 146C. Oldest stems: RHS 156D flushed with RHS 160D.

*Appearance (shape).*—Columnar, cylindrical upright.

*Aspect.*—Vertical, upright.

*Strength.*—Sturdy, somewhat flexible.

*Axillary buds.*—Shape: Elliptic, flat. Length: 0.40 cm. Width: 0.20 cm. Color: RHS 158D.

*Branch sports.*—Several are produced having stems, petioles, leaf midribs, and petiole sheaths; all are RHS 148A to RHS 146A, spotted with RHS 160C tinged with RHS 49D.

Leaves:

*Arrangement.*—Alternate, single, arranged in a spiral along the stem.

*Quantity of leaves per stem.*—9.

*Quantity of leaflets per leaf.*—Single, simple.

*Young leaf (Newly expanded leaf).*—Color: Upper side: Base color RHS 147A to RHS N189A; RHS 147A to RHS 191A (dark silver-green) areas follow the primary veins; RHS 146D to RHS 150D (yellow-green) spots; RHS 150D to RHS 146D areas adjacent to the midrib and often tinged with RHS 51C. Under side: Base color lighter than, but closest to RHS N186C with a cast of RHS 147A (dark-green), with spots of RHS 181C; areas adjacent to the primary veins and midrib are RHS 181C.

*Mature leaf.*—Color: Upper side: Base color darker than, but closest to RHS N189A to RHS 147A (dark-green); RHS 147A to RHS 191A (dark silver-green) areas which follow the primary veins; RHS 146D to RHS 150D (yellow-green) spots; areas adjacent to the midrib are RHS 150D to RHS 146D and often variably tinged with RHS 51C. Under side: RHS N186C base color with RHS 147A (dark-green) cast, with spots of RHS 181C; areas adjacent to the primary veins and midrib are RHS 181C.

*Length.*—14.5 cm to 17.0 cm.

*Width.*—Flattened: 9.5 cm to 10.8 cm. Not flattened: 7.5 cm to 9.0 cm; the leaf blade folds upward along the midrib.

*Shape.*—Ovate to elliptic.

*Apex.*—Acuminate to acute.

*Base.*—Obtuse.

*Margin.*—Smooth, entire; mostly flat with some broad undulations.

*Texture.*—Smooth; new leaves shiny; mature leaves glossy; the leaf blade is convex between the main veins resulting in a textured appearance.

*Pubescence.*—Absent.

*Venation pattern.*—Pinnate, radiating outward from the midrib in a herringbone arrangement.

*Venation color (newly expanded leaf).*—Upper side: Primary veins: RHS 51B Midrib: RHS 51B to RHS 51D, streaked with RHS 146C. Under side: Primary veins: RHS 181C. Midrib: RHS 181C to RHS 181D.

*Venation color (mature leaf).*—Upper side: Primary veins: RHS 51B to RHS 49A. Midrib: RHS 51B to RHS 53C streaked with RHS 146C (green). Under side: Primary veins: RHS 181C to RHS 181D. Midrib: RHS 181C.

Petioles:

*Aspect.*—Vertical upright when newly expanded, becoming curved outward and about 45° with maturity.

*Length.*—7.8 cm.

*Diameter.*—Distal: 0.4 cm. Proximal (petiole and petiole sheath clasps the stem proximally): Flattened: 2.6 cm. Natural diameter: 0.95 cm.

*Color.*—Distal: RHS 181D flushed with RHS 50C (between the top of the wing and the base of the leaf. Proximal: RHS 49C flushed with RHS 47D. Area adjacent to stem: RHS 49D.

*Wing length.*—6.8 cm.

*Wing diameter.*—Mid-point: 0.65 cm. Base: 0.95 cm. Depth: 0.70 cm.

*Wing color.*—Inside: RHS 49D flushed with RHS 49A. Outside: RHS 49D flushed with RHS 47C to RHS 47D. Area adjacent to stem: RHS 49D.

*Cataphylls.*—Length: 4.9 cm. Width: 1.1 cm. Shape: Linear to lanceolate, two-keeled, translucent. Texture: Smooth. Color: RHS 159C tinged with RHS 50C.

Inflorescence:

*Appearance.*—Hooded spathes surrounding a columnar spadix borne atop an upright peduncle; monoecious; spadix a central column of sessile, simple male and female flowers separated into two zones; male flowers occupy the upper two-thirds of the spadix, female flowers the lower one-third.

*Arrangement.*—2 to 3 inflorescences per stem, persistent.

*Aspect.*—Upright.

*Height (from base of peduncle to tip of spathe).*—13 cm.

*Diameter/width.*—7.0 cm.

*Flowering habit.*—Seasonal, summer and fall as observed in Apopka, Fla.

*Number of inflorescences per plant.*—5.

*Lastingness of inflorescences on the plant.*—Not observed.

*Fragrance.*—None

*Ratio of inflorescence opening.*—About 1 new flower every 10–14 days.

*Peduncle.*—Length: 10.1 cm. Diameter: 0.45 cm. Angle: Upright. Strength: Sturdy, flexible. Color: RHS 160C to RHS 160D.

Spathe:

*Appearance.*—Simple, hooded, cupped, enclosing spadix.

*Arrangement.*—Upright.

*Shape.*—Elliptic.

*Apex.*—Acute.

*Margin.*—Entire.

*Texture.*—Smooth, shiny.

*Size.*—Length: 7.0 cm. Width: 2.2 cm.

*Color (fully opened).*—Front side: RHS 145C. Rear side: RHS 145C with sparse speckles of RHS 145A.

Spadix:

*Appearance.*—Columnar.

*Size.*—Length: 3.3 cm. Diameter (female zone): 0.7 cm. Diameter (male zone): 0.6 cm. Length of female zone: 1.2 cm. Length of male zone: 2.1 cm.

*Arrangement/aspect.*—Upright.

*Shape.*—Columnar.

*Apex.*—Obtuse.

*Base.*—Obtuse.

*Margin.*—Entire,

*Color.*—Female zone: RHS 7D. Male zone: RHS 2D.

Flowers:

*Type.*—Simple, individual flowers reduced to the most basic elements.

*Quantity of female flowers per spadix.*—19.

*Quantity of male flowers per spadix.*—270.

*Shape of female.*—Ovate to elliptic.

*Shape of male.*—Obovate, inverted triangle.

*Size.*—Female width: 0.2 cm. Female height: 0.2 cm. Male width: 0.10 cm. Male height: 0.22 cm.

Reproductive organs:

*Stigma color.*—RHS 7D.

*Ovary color.*—RHS 159D.

*Fruit and Seed Set.*—None observed.

Disease and insect resistance: Typical of the species.

COMPARISON WITH KNOWN CULTIVARS

'TWYAG0004' differs from the commercial variety 'Dynamic Ruby' (U.S. Plant Pat. No. 14,137) in that 'TWYAG0004' has a taller and wider growth habit and lacks fragrance whereas 'Dynamic Ruby' has fragrance.

'TWYAG0004' differs from the female parent, *A. commutatum* var. *tricolor* (unpatented), in that 'TWYAG0004' has ovate to elliptic leaves with maroon undersides and dark pink petioles while *A. commutatum* var. *tricolor* has elliptic to oblong leaves with pale yellow-green undersides and pale pink petioles.

'TWYAG0004' differs from the male parent, *A. rotundum* (unpatented), in that 'TWYAG0004' has leaves with lateral yellow veins which are tinted red while *A. rotundum* has leaves with lateral veins which are red or pinkish red. In addition, 'TWYAG0004' has ovate to elliptic leaves with maroon undersides and pale venation while *A. rotundum* has ovate leaves with maroon undersides which lack visible venation.

I claim:

1. A new and distinct cultivar of *Aglaonema* plant as shown and described herein.

* * * * *